United States Patent
Barak (10) Patent No.: US 9,801,384 B2
(45) Date of Patent: Oct. 31, 2017

(54) METHOD FOR CONTROLLING THE PRODUCTION OF A BIOCIDE

(71) Applicant: A.Y. LABORATORIES LTD., Tel Aviv (IL)

(72) Inventor: Ayala Barak, Tel Aviv (IL)

(73) Assignee: A.Y. LABORATORIES LTD., Tel Aviv (IL)

( * ) Notice: Subject to any disclaimer, the term of this patent is extended or adjusted under 35 U.S.C. 154(b) by 214 days.

(21) Appl. No.: 14/765,335

(22) PCT Filed: Feb. 6, 2014

(86) PCT No.: PCT/IL2014/050130
§ 371 (c)(1),
(2) Date: Aug. 1, 2015

(87) PCT Pub. No.: WO2014/122652
PCT Pub. Date: Aug. 14, 2014

(65) Prior Publication Data
US 2015/0367315 A1    Dec. 24, 2015

Related U.S. Application Data

(60) Provisional application No. 61/761,922, filed on Feb. 7, 2013.

(51) Int. Cl.
*C01B 11/06* (2006.01)
*A01N 59/00* (2006.01)
(Continued)

(52) U.S. Cl.
CPC .......... *A01N 59/00* (2013.01); *B01J 19/0006* (2013.01); *C01B 11/06* (2013.01); *C02F 1/76* (2013.01);
(Continued)

(58) Field of Classification Search
CPC .................. C01B 11/06; B01J 19/0033; B01J 2219/00177; B01J 2219/00164;
(Continued)

(56) References Cited

U.S. PATENT DOCUMENTS 5,976,386 A * 11/1999 Barak ....................... C02F 1/50
210/101
6,132,628 A   10/2000 Barak
(Continued)

FOREIGN PATENT DOCUMENTS

AU   2008202149   11/2008
CN   101151219   3/2008
(Continued)

OTHER PUBLICATIONS

European Search Report dated Oct. 26, 2015, which issued during the prosecution of Applicant's European App No. 14749041.1.
(Continued)

*Primary Examiner* — Wayne Langel
(74) *Attorney, Agent, or Firm* — Koffsky Schwalb LLC; Mark I. Koffsky (57) ABSTRACT

A method and apparatus for producing a biocide from a hypochlorite oxidant and an ammonium salt are provided. The method includes monitoring a control parameter to optimize the ratio between the hypochlorite oxidant and the ammonium salt. The control parameter may be oxidation-reduction potential, conductivity, induction or oxygen saturation.

32 Claims, 1 Drawing Sheet

(51) Int. Cl.
*B01J 19/00* (2006.01)
*C02F 1/76* (2006.01)

(52) U.S. Cl.
CPC .............. *B01J 2219/0018* (2013.01); *B01J 2219/00049* (2013.01); *C02F 2209/04* (2013.01); *C02F 2209/055* (2013.01); *C02F 2209/06* (2013.01); *C02F 2209/22* (2013.01)

(58) Field of Classification Search
CPC .. B01J 2219/00245; B01J 2219/00186; A01N 59/00
See application file for complete search history.

(56) References Cited

U.S. PATENT DOCUMENTS

| | | | |
|---|---|---|---|
| 2005/0147528 A1* | 7/2005 | Shim | A01N 59/00 422/37 |
| 2005/0233900 A1* | 10/2005 | Smith | A01N 59/00 502/407 |
| 2006/0154978 A1 | 7/2006 | Barak | |
| 2006/0231505 A1* | 10/2006 | Mayer | A01N 59/00 210/764 |
| 2007/0045199 A1* | 3/2007 | Mayer | A01N 59/00 210/764 |
| 2007/0049642 A1* | 3/2007 | Singleton | A01N 59/00 514/612 |
| 2007/0123423 A1* | 5/2007 | Cheng | A01N 59/00 504/116.1 |
| 2009/0311164 A1* | 12/2009 | Gupta | C01B 21/091 423/413 |
| 2011/0142959 A1 | 6/2011 | Farone et al. | |
| 2011/0159117 A1 | 6/2011 | Mayer et al. | |
| 2012/0021062 A1 | 1/2012 | Gupta et al. | |
| 2012/0328504 A1 | 12/2012 | Debiemme-Chouvy | |
| 2013/0302443 A1* | 11/2013 | Janak | D21C 9/08 424/657 |

FOREIGN PATENT DOCUMENTS

| | | |
|---|---|---|
| CN | 101933510 | 1/2011 |
| JP | H3-42095 | 2/1991 |
| JP | H10-506835 | 7/1998 |
| JP | 2001-259652 | 9/2001 |
| JP | 2007-526244 | 9/2007 |
| JP | 2008-264615 | 11/2008 |
| JP | 2009-95742 | 5/2009 |
| JP | 2013-22541 | 2/2013 |
| WO | 2014/122652 | 8/2014 |

OTHER PUBLICATIONS

European Search Reported dated Jan. 21, 2016 which issued during the prosecution of Applicant's European App No. 14749041.1.
U.S. Appl. No. 61/761,922, filed Feb. 7, 2013.
An International Search Report and a Written Opinion both dated May 23, 2014, which issued during the prosecution of Applicant's PCT/IL2014/050130.
An International Preliminary Report on Patentability dated Aug. 11, 2015, which issued during the prosecution of Applicant's PCT/IL2014/050130.
An English Translation of an Office Action dated Jan. 21, 2016, which issued during the prosecution of Korean Patent Application No. 10-2014-7004862.
An English Translation of an Office Action dated Apr. 22, 2016, which issued during the prosecution of Korean Patent Application No. 10-2014-7004862.
An English Translation of an Office Action dated Aug. 9, 2016, which issued during the prosecution of Korean Patent Application No. 10-2014-7004862.
An English Translation of an Office Action dated Aug. 12, 2016, which issued during the prosecution of Korean Patent Application No. 10-2016-7007128.
An English Translation of an Office Action dated Jul. 19, 2016, which issued during the prosecution of Chinese Patent Application No. 201480008446.7.
An Office Action dated Mar. 28, 2017, which issued during the prosecution of Japanese Patent Application No. 2015-556617.
Notice of Allowance dated Mar. 29, 2017, which issued during the prosecution of Korean Patent Application No. 10-2016-7007128.

\* cited by examiner

METHOD FOR CONTROLLING THE PRODUCTION OF A BIOCIDE

CROSS-REFERENCE TO RELATED APPLICATIONS

This application is a National Phase Application of PCT International Application No. PCT/IL2014/05130, International Filing Date Feb. 6, 2014, entitled METHOD FOR CONTROLLING THE PRODUCTION OF A BIOCIDE, which claims priority to U.S. Provisional Patent Application Ser. No. 61/761,922, filed Feb. 7, 2013 and entitled METHOD FOR CONTROLLING THE PRODUCTION OF A BIOCIDE, the disclosures of which are hereby incorporated by reference.

Reference is made to U.S. patent application Ser. No. 07/892,533, filed Jun. 1, 1992 and entitled PROCESS AND COMPOSITIONS FOR THE DISINFECTION OF WATERS, U.S. patent application Ser. No. 08/809,346, filed Jan. 27, 1998 and entitled METHOD AND APPARATUS FOR TREATING LIQUIDS TO INHIBIT GROWTH OF LIVING ORGANISMS, and U.S. patent application Ser. No. 10/586,349, filed Jul. 14, 2006 and entitled BIOCIDES AND APPARATUS, the disclosures of which are hereby incorporated by reference.

FIELD OF THE INVENTION

The present invention relates to a method for controlling and optimizing the production of a biocide.

BACKGROUND OF THE INVENTION

Various techniques are known for producing and using biocides.

SUMMARY OF THE INVENTION

The present invention seeks to provide a method and apparatus for controlling and optimizing the production of a biocide.

There is thus provided in accordance with a preferred embodiment of the present invention a method for producing a biocide including: mixing a solution of a hypochlorite oxidant with a solution of an ammonium salt; and monitoring a control parameter that indicates when a maximum yield of the biocide, which yield is attainable without degradation of the biocide, has been reached; wherein the control parameter is not pH. Preferably, the hypochlorite oxidant is sodium hypochlorite.

In accordance with a preferred embodiment of the present invention, the solution of a hypochlorite oxidant is prepared by diluting a commercial stock solution of about 8-18% with water immediately prior to use. Preferably, the solution of a hypochlorite oxidant has a concentration from about 1000 to about 20,000 ppm, more preferably from about 3000 to about 10,000 ppm, and most preferably from about 3000 to about 6000 ppm.

In accordance with a preferred embodiment of the present invention, the ammonium salt is selected from ammonium bicarbonate, ammonium carbonate, ammonium carbamate, ammonium hydroxide, ammonium sulfamate, ammonium bromide, ammonium chloride and ammonium sulfate. Preferably, the ammonium salt is selected from ammonium carbonate, ammonium carbamate, ammonium sulfamate, ammonium bromide, ammonium chloride and ammonium sulfate. More preferably, the ammonium salt is selected from ammonium carbonate, ammonium carbamate and ammonium sulfamate. Most preferably, the ammonium salt is selected from ammonium carbonate and ammonium carbamate.

In accordance with a preferred embodiment of the present invention, the solution of an ammonium salt is prepared by diluting a commercial stock solution of about 15-50% with water or with the solution of a diluted hypochlorite oxidant immediately prior to use. Preferably, the solution of an ammonium salt has a concentration from about 1,000 to about 50,000 ppm, more preferably, from about 12,000 to about 30,000 ppm. In accordance with a preferred embodiment of the present invention, the solution of an ammonium salt further includes a base. Preferably, the base is sodium hydroxide.

Preferably, the control parameter is selected from oxidation-reduction potential (ORP), conductivity, induction, total dissolved solids (TDS), oxygen concentration and oxygen saturation. In one embodiment, the control parameter is ORP. In an alternative embodiment, the control parameter is conductivity, induction or TDS. In a still further embodiment, the control parameter is oxygen concentration or oxygen saturation.

In accordance with a preferred embodiment of the present invention, the method includes: providing a discrete amount of the solution of an ammonium salt; and adding a plurality of discrete amounts of the solution of a hypochlorite oxidant to the discrete amount of the solution of an ammonium salt under mixing conditions; and measuring the control parameter after the addition of each discrete amount of the solution of a hypochlorite oxidant. Alternatively, a plurality of discrete amounts of an ammonium salt solution are added to a discrete amount of a hypochlorite solution under mixing conditions while measuring the control parameter.

In accordance with another preferred embodiment of the present invention, the method includes: mixing a stream of a hypochlorite solution with a stream of an ammonium salt solution in a mixing chamber at a starting ratio; holding the flow rate of one of the streams constant and gradually increasing or decreasing the flow rate of the other of the streams; and monitoring the value of the control parameter in a stream leaving the mixing chamber. In one embodiment, the monitoring is continuous. In an alternative embodiment, the monitoring includes measuring the control parameter in discrete samples of the stream leaving the mixing chamber.

There is also provided in accordance with another preferred embodiment of the present invention a method of producing a biocide, including: providing a solution of a hypochlorite oxidant; providing a solution of an ammonium salt; diluting the solution of an ammonium salt with a portion of the solution of a hypochlorite oxidant to form an ammonium salt dilution; and mixing the remainder of the solution of a hypochlorite oxidant with the ammonium salt dilution. Preferably, the hypochlorite oxidant is sodium hypochlorite.

In accordance with a preferred embodiment of the present invention, the solution of a hypochlorite oxidant is prepared by diluting a commercial stock solution of about 8-18% with water immediately prior to use. Preferably, the solution of a hypochlorite oxidant has a concentration from about 2000 to about 20,000 ppm, more preferably from about 3000 to about 10,000 ppm, and most preferably from about 3000 to about 6000 ppm.

In accordance with a preferred embodiment of the present invention, the ammonium salt is selected from ammonium bicarbonate, ammonium carbonate, ammonium carbamate, ammonium hydroxide, ammonium sulfamate, ammonium bromide, ammonium chloride and ammonium sulfate. Preferably, the ammonium salt is selected from ammonium carbonate, ammonium carbamate, ammonium sulfamate, ammonium bromide, ammonium chloride and ammonium sulfate. More preferably, the ammonium salt is selected from ammonium carbonate, ammonium carbamate and ammonium sulfamate. Most preferably, the ammonium salt is selected from ammonium carbonate and ammonium carbamate.

In accordance with a preferred embodiment of the present invention, the solution of an ammonium salt is prepared by diluting a commercial stock solution of about 15-50% with water or with the solution of a hypochlorite oxidant immediately prior to use. Preferably, the solution of an ammonium salt has a concentration from about 1,000 to about 50,000 ppm, more preferably, from about 12,000 to about 30,000 ppm.

In accordance with a preferred embodiment of the present invention, the solution of an ammonium salt further includes a base. Preferably, the base is sodium hydroxide. In accordance with a preferred embodiment of the present invention, the portion of the solution of a hypochlorite oxidant used to dilute the solution of an ammonium salt is about 10% to about 50% of the solution of a hypochlorite oxidant.

Preferably, the method further includes monitoring a control parameter that indicates when a maximum yield of the biocide, which yield is attainable without degradation of the biocide, has been reached. Preferably, the control parameter is selected from oxidation-reduction potential (ORP), conductivity, induction, TDS, oxygen concentration and oxygen saturation. In one embodiment, the control parameter is ORP. In an alternative embodiment, the control parameter is conductivity, induction or TDS. In a still further embodiment, the control parameter is oxygen saturation or oxygen concentration.

In accordance with a preferred embodiment of the present invention, the method includes: adding a plurality of discrete amounts of the solution of a hypochlorite oxidant to the ammonium salt dilution under mixing conditions; and measuring the control parameter after the addition of each discrete amount of the solution of a hypochlorite oxidant.

In accordance with another preferred embodiment of the present invention, the method includes: mixing a stream of a hypochlorite solution with a stream of the ammonium salt dilution in a mixing chamber at a starting ratio; holding the flow rate of one of the streams constant and gradually increasing or decreasing the flow rate of the other of the streams; and monitoring the value of the control parameter in a stream leaving the mixing chamber. In one embodiment, the monitoring is continuous. In another embodiment, the monitoring includes measuring the control parameter in discrete samples of the stream leaving the mixing chamber.

There is also provided in accordance with another preferred embodiment of the present invention an apparatus for producing a biocide including: a reservoir containing a solution of a hypochlorite oxidant; a reservoir containing a solution of an ammonium salt; a mixing chamber for mixing the hypochlorite oxidant with the ammonium salt to form a biocide; and a control cell for monitoring a control parameter of the biocide that indicates when a maximum yield of the biocide, which yield is attainable without degradation of the biocide, has been reached; wherein the control parameter is not pH. Preferably, the hypochlorite oxidant is sodium hypochlorite.

In accordance with a preferred embodiment of the present invention, the apparatus further includes a water source; and a conduit wherein the solution of a hypochlorite oxidant is mixed with the water to form a hypochlorite dilution, the conduit coupled to the mixing chamber. Preferably, the apparatus further includes a conduit wherein the solution of an ammonium salt is mixed with the water or with the hypochlorite dilution to form an ammonium salt dilution, the conduit coupled to the mixing chamber.

Preferably, the ammonium salt is selected from ammonium bicarbonate, ammonium carbonate, ammonium carbamate, ammonium hydroxide, ammonium sulfamate, ammonium bromide, ammonium chloride and ammonium sulfate. More preferably, the ammonium salt is selected from ammonium carbonate, ammonium carbamate, ammonium sulfamate, ammonium bromide, ammonium chloride and ammonium sulfate. In accordance with a preferred embodiment of the present invention, the solution of an ammonium salt further includes a base. Preferably, the base is sodium hydroxide.

Preferably, the control parameter is selected from oxidation-reduction potential (ORP), conductivity, induction, TDS, oxygen concentration and oxygen saturation. In one embodiment, the control parameter is ORP. In an alternative embodiment, the control parameter is conductivity, induction or TDS. In a still further embodiment, the control parameter is oxygen saturation or oxygen concentration.

In accordance with a preferred embodiment of the present invention, the apparatus further includes a control unit configured to: hold the flow rate of one of the hypochlorite oxidant and the ammonium salt constant and gradually increase or decrease the flow rate of the other one of the hypochlorite oxidant and the ammonium salt; monitor the value of the control parameter of the biocide; and adjust the flow rate of the hypochlorite oxidant or the ammonium salt to attain a maximum yield of the biocide, which yield is attainable without degradation of the biocide.

There is also provided in accordance with another preferred embodiment of the present invention an apparatus for producing a biocide including: a reservoir containing a solution of a hypochlorite oxidant; a reservoir containing a solution of an ammonium salt; a water source; a conduit for mixing the solution of a hypochlorite oxidant solution with the water to form a hypochlorite dilution; a conduit for mixing the solution of an ammonium salt with a portion of the hypochlorite dilution to form an ammonium salt dilution; and a mixing chamber for mixing a portion of the hypochlorite dilution with the ammonium salt dilution to form a biocide. Preferably, the hypochlorite oxidant is sodium hypochlorite.

Preferably, the ammonium salt is selected from ammonium bicarbonate, ammonium carbonate, ammonium carbamate, ammonium hydroxide, ammonium sulfamate, ammonium bromide, ammonium chloride and ammonium sulfate. More preferably, the ammonium salt is selected from ammonium carbonate, ammonium carbamate, ammonium sulfamate, ammonium bromide, ammonium chloride and ammonium sulfate. In accordance with a preferred embodiment of the present invention, the solution of an ammonium salt further includes a base. Preferably, the base is sodium hydroxide. Preferably, the portion of the hypochlorite dilution mixed with the solution of an ammonium salt is about 10% to about 50% of the solution of a hypochlorite oxidant.

In accordance with a preferred embodiment of the present invention, the apparatus further includes a control cell for monitoring a control parameter of the biocide that indicates when a maximum yield of the biocide, which yield is attainable without degradation of the biocide, has been reached. Preferably, the control parameter is selected from oxidation-reduction potential (ORP), conductivity, induction, TDS, oxygen concentration and oxygen saturation. In one embodiment, the control parameter is ORP. In an alternative embodiment, the control parameter is conductivity, induction or TDS. In a still further embodiment, the control parameter is oxygen saturation or oxygen concentration.

In accordance with a preferred embodiment of the present invention, the apparatus further includes a control unit configured to: hold the flow rate of one of the hypochlorite dilution and the ammonium salt dilution constant and gradually increase or decrease the flow rate of the other one of the hypochlorite dilution and the ammonium salt dilution; monitor the value of the control parameter of the biocide; and adjust the flow rate of the hypochlorite dilution or the ammonium salt dilution to attain a maximum yield of the biocide, which yield is attainable without degradation of the biocide.

BRIEF DESCRIPTION OF THE DRAWING

The Present Invention Will be Understood and Appreciated More Fully from the Following Detailed Description, Taken in Conjunction with the Drawing in which.

DETAILED DESCRIPTION OF THE INVENTION

As described in published European Patent Publication No. 0 517 102, the contents of which are incorporated herein by reference, biological fouling of circulating water is a well known problem caused by algae, fungi, bacteria, and other simple life forms found in circulating water. That patent publication describes controlling biofouling in high chlorine demand waters by mixing two components, one of which is an oxidant and the other an ammonium salt, and adding the mixture substantially immediately to the aqueous system to be treated. This produces the active biocidal ingredient, as described therein. A large number of examples of oxidants and ammonium salts are described in that patent publication.

A problem encountered in this method of treating liquid to inhibit growth of living organisms, however, is that the concentrated active biocidal ingredient is extremely non-stable chemically and quickly decomposes upon formation with the result that there is a fast drop in pH. This is especially so for the active biocidal ingredients derived from ammonium bromide where the decomposition results in the undesirable formation of HOBr. Therefore, when conventional dosing pumps and mixers are used, the formed active biocidal ingredient quickly decomposes and loses its efficacy. Also, while the pH range of such concentrated active biocide is theoretically 8.0-12.5, actually the pH never exceeds 8.0 because of the fast decomposition. In addition, the ammonium salts must be supplied in excess in order to decrease the decomposition rate.

In U.S. Pat. No. 5,976,386, the contents of which are incorporated herein by reference, a method and apparatus for producing a biocide are disclosed that enable a constant ratio of oxidant/amine source to be maintained, thereby avoiding the need to use excess amine source in order to stabilize the reaction product and to maintain a reproducible product containing almost no degradation products. The novel method described therein includes producing an efficient in situ dilution of both the oxidant and the amine source and synchronously metering the two dilutions into a conduit to continuously mix therein according to a predetermined ratio to produce an active biocidal ingredient.

As already described in U.S. Pat. No. 5,976,386, careful control of the biocide formation is necessary. The biocide production process uses a multiple feeding point system requiring a separate control for each feed line since different pumps respond differently to pressure change, and pump feed rates depend on the water flow pressure. As for any on-site process, an online control is needed to ensure production of the right product at high yield, and with minimal side products. Furthermore, as shown in the above referenced patents, equimolar amounts of ammonium and hypochlorite are necessary for optimal performance. Excess hypochlorite, even local excess, leads to production of multi-chlorinated chloramines and degradation of the biocidal product monochloramine (MCA) to form $NO_x$ species and inorganic acids. With insufficient hypochlorite, the ammonium does not fully react, leading to a lower biocide concentration, excessive use of chemicals, higher cost of treatment, etc. The components used to make the biocide, such as sodium hypochlorite and ammonium carbamate, disclosed in U.S. Pat. No. 7,837,883, the contents of which are incorporated herein by reference, are unstable chemicals, and degrade with time during use. As a result, operating the feeding unit under predetermined constant feed rates of the two reagents will produce variable products. In addition, other parameters such as water temperature, high concentration of the produced biocide can water quality can enhance degradation of the biocide and cause the biocide to degrade before the 1:1 equimolar ratio has been reached.

Thus, there is a need to maintain the system at the equimolar point or the point of highest possible biocide yield with no degradation by continuously monitoring the reaction online and making the needed changes in the process to maintain equimolarity or no degradation under changing conditions (e.g., reagent concentration, different feeding points, changes in dilution water quality, changes in temperature of dilution water, etc). Defining an end point for the reaction is also crucial for making the biocide in the field.

In U.S. Pat. No. 5,976,386 is disclosed the use of pH as an indicator of the end point of the reaction between an ammonium salt and sodium hypochlorite. Addition of hypochlorite to an ammonium salt solution increases the pH. However, after the equimolar point, the hypochlorite begins to degrade the biocidal MCA forming inorganic acids, which lower the pH. Thus, pH can be used as an indicator of the end point.

However, the effect of the degradation of MCA on pH is only noticeable at a pH up to about 10.5. Above pH 10.5, the amount of acid necessary to noticeably lower the pH is so high, that a significant excess of hypochlorite must be added before the pH change is observed. Accordingly, pH loses its sensitivity to degradation of the MCA and is not a reliable indicator of the end point at high pH. Some ammonium salts, such as ammonium carbamate, are stable only at high pH levels or high alkalinity which dictates production of the biocide at a high pH and, therefore, additional end point indicators for production of MCA at high pH are necessary.

It is known to use pH and oxidation-reduction potential (ORP) to monitor chlorine demand during water disinfection. See, for example,
a. Devkota et al., "Variation of Oxidation-Reduction Potential Along the Breakpoint Curves in Low-Ammonia Effluents", Water Environment Research 2000, 72(5):610-617;
b. Karanfil et al., "Analysis of disinfection difficulties in two municipal water pollution control plants", Disinfection '98: The Latest Trends in Wastewater Disinfection: Chlorination vs. UV Disinfection, Proceedings, Baltimore, Apr. 19-22, 1998, 111-122;

c. Kim et al., "New process control strategy for wastewater chlorination and dechlorination using ORP/pH", Water Sci Technol. 2006; 53(4-5):431-438;

d. Kopchynski et al., "Comparisons of on-line ORP and chlorine residual monitoring/control systems for wastewater treatment plant final effluent chlorination", Conference Proceedings—Water Environment Federation Annual Conference & Exposition, 74th, Atlanta, Ga., United States, Oct. 13-17, 2001, 4275-4295; and e. Yu, "Feed-forward dose control of wastewater chlorination using on-line pH and ORP titration", Chemosphere. 2004 September, 56(10):973-980.

Other monitoring methods, such as colorimetric analysis are also known. See, for example, f. Harp, "Specific Determination of Inorganic Monochloramine in Chlorinated Wastewaters", Water Environment Research 2000, 72(6): 706-713;

g. Kobylinski et al., "On Line Control Strategies for Disinfection Systems: Success and Failure" Proceedings of the Water Environment Federation, WEFTEC 2006: Session 81 through Session 94, pp. 6371-6394; and h. Pollema, "Monitoring Monochloramine, Total Ammonia, and Free Ammonia in the Chlorination of Treated Wastewater", Proceedings of the Water Environment Federation, Disinfection 2000, pp. 168-181.

Woodward et al., "Relationships between observed monochloramine decay rates and other physical and chemical parameters in a large scale experimental pipe system", Proceedings—Water Quality Technology Conference (1996), Volume Date 1995, (Pt. 1), 935-949 discloses the use of oxygen concentration in addition to ORP to monitor the concentration of chlorine species in water distribution systems. U.S. Pat. No. 8,012,758 discloses the use of dissolved oxygen to measure microbiological activity. There does not appear to be any report of using a control parameter other than pH for producing a monochloramine biocide at a maximum yield, which can be obtained without degradation of the biocide.

In accordance with a first embodiment of the present invention, there is provided a method for producing a biocide comprising mixing a solution of a hypochlorite oxidant with a solution of an ammonium salt and monitoring a control parameter that can indicate the proper ratio of hypochlorite to ammonium salt in order to produce the maximum amount of biocide without degrading the biocide.

In one embodiment, the biocide is produced in a batch process. The batch process comprises adding a solution of a hypochlorite oxidant to a solution of an ammonium salt while mixing, monitoring a control parameter that can indicate that all of the ammonium salt has reacted, or that the biocide has begun to degrade and ceasing the addition of the solution of hypochlorite when the control parameter indicates that all of the ammonium salt has reacted. The biocide so produced can be used immediately or stored for later use. During storage, monitoring of the control parameter can be continued to ensure biocide quality and to determine the point in time when the biocide must be used or else it will degrade.

In an alternative embodiment, the biocide is produced in a continuous process. In the continuous process, a solution of hypochlorite and a solution of ammonium salt are mixed continuously in a mixer, and a control parameter is monitored online in the mixer or in a conduit downstream from the mixer or is measured in discrete samples removed from the mixer. The flow rate of one of the solutions is held constant while the flow rate of the other solution is varied until the control parameter indicates that the optimum ratio of flow rates has been reached to produce the biocide at the highest yield possible without degradation. Typically, monitoring of the control parameter is continued in order to identify the need to adjust the flow rates as a result of a change in the concentration of one of the solutions. The biocide produced in the continuous process can be applied to a medium as it is produced or can be stored for later use.

The hypochlorite oxidant can be any hypochlorite oxidant, such as the hypochlorite salt of an alkali metal or alkaline earth metal. Preferably, the hypochlorite salt is sodium hypochlorite, potassium hypochlorite or calcium hypochlorite. Most preferably, the hypochlorite salt is sodium hypochlorite.

The hypochlorite solution is preferably prepared by mixing a concentrated stock solution of hypochlorite with water to form a hypochlorite dilution. The ammonium salt solution is preferably prepared by mixing a concentrated stock solution of the ammonium salt with water or with the hypochlorite dilution to form an ammonium salt dilution. When the ammonium stock solution is diluted with water to prepare an ammonium salt dilution that is equimolar with the hypochlorite dilution, the final concentration of the biocide will be half the concentration of the hypochlorite dilution. On the other hand, when the ammonium stock solution is diluted with the hypochlorite dilution, the final concentration of the biocide will be equal to the concentration of the hypochlorite dilution.

The concentration of the hypochlorite dilution is preferably from about 1000 to about 20,000 ppm. More preferably, the concentration of the hypochlorite solution is from about 3000 to about 10,000 ppm. Most preferably, the concentration of the hypochlorite solution is from about 3500 to about 7000 ppm. The hypochlorite solution is preferably prepared by diluting a commercial stock solution of about 8-18% with water immediately prior to use. Preferably, the hypochlorite dilution is prepared immediately before use. When the biocide is formed in a continuous process, the hypochlorite dilution is preferably prepared online as it is needed.

Any ammonium salt can be used in the method of the present invention. Preferably, the ammonium salt is selected from ammonium bicarbonate, ammonium bromide, ammonium carbamate, ammonium carbonate, ammonium chloride, ammonium hydroxide, ammonium sulfamate and ammonium sulfate. More preferably, the ammonium salt is selected from ammonium bromide, ammonium carbamate, ammonium carbonate, ammonium chloride, ammonium sulfamate and ammonium sulfate. Even more preferably, the ammonium salt is selected from ammonium carbamate, ammonium carbonate and ammonium sulfamate. Most preferably, the ammonium salt is ammonium carbamate.

In one embodiment, the ammonium salt dilution is prepared by diluting a 15-50% stock solution of the ammonium salt in water to a concentration of about 1,000 to about 50,000 ppm, more preferably, about 12,000 to about 30,000 ppm. Preferably, the ammonium salt dilution is prepared immediately before use. When the biocide is formed in a continuous process, the ammonium salt dilution is preferably prepared online as it is needed.

In an alternative embodiment, the ammonium salt dilution is prepared by diluting the stock solution of the ammonium salt with a portion of the diluted hypochlorite solution. This method produces an ammonium salt dilution with a higher pH since the hypochlorite solution is basic. This is advantageous for some salts, such as ammonium carbamate, which are more stable at high pH.

In some embodiments, the initial pH of the ammonium salt dilution is preferably at least 9.0, more preferably at least 10.0, even more preferably at least 10.4, and most preferably at least 10.8. In one preferred embodiment, the ammonium salt dilution comprises sodium hydroxide.

The control parameter can be any parameter that has a) a fixed value that will change only if and when the ammonium salt has been exhausted and degradation of the monochloramine product starts; or b) a variable value that has a maximum, a minimum or an inflection at the point that the ammonium salt has been exhausted and degradation of the monochloramine product starts. For example, the value of the control parameter increases gradually when the hypochlorite to ammonium salt ratio increases as the biocide is produced, but begins to decrease gradually once degradation occurs. At the end point of production of the biocide, and just before the beginning of degradation a maximum value is measured. Immediately as degradation starts, the measured values are decreasing. Even if the absolute value of the control parameter depends on conditions such as concentration, water quality, temperature, etc., there will be a relative maximum value measured just before the biocide starts to degrade.

The value of the control parameter must be easy to measure reliably and should be sensitive to reaction conditions. Preferably, the control parameter is selected from oxidation-reduction potential (ORP), conductivity and dissolved oxygen saturation. Both ORP and conductivity reach a minimum at the end point. Conductivity is essentially a measure of the ion concentration. Induction and total dissolved solids (TDS) are also measures of ion concentration and can be used in place of conductivity as a control parameter. Any other measure of ion concentration can also be used.

Oxygen saturation is close to 100% throughout the formation of the biocide. Once the end point has been reached and degradation of MCA begins, the oxygen saturation begins to drop as the degrading biocide reacts with oxygen to form $NO_x$ species. The drop in saturation is slow at the beginning, but at a certain point the saturation falls quickly to zero. An oxygen saturation of less than 90% is indicative of degradation. The point at which the oxygen saturation begins to drop quickly can be used to determine the endpoint. In some embodiments, two or more control parameters selected from ORP, conductivity and oxygen saturation are used. In other embodiments, all of ORP, conductivity and oxygen saturation are used as control parameters. Oxygen concentration can also be used as a control parameter. Oxygen saturation is preferred since it accounts for changes in temperature of the solution.

Figure 1:
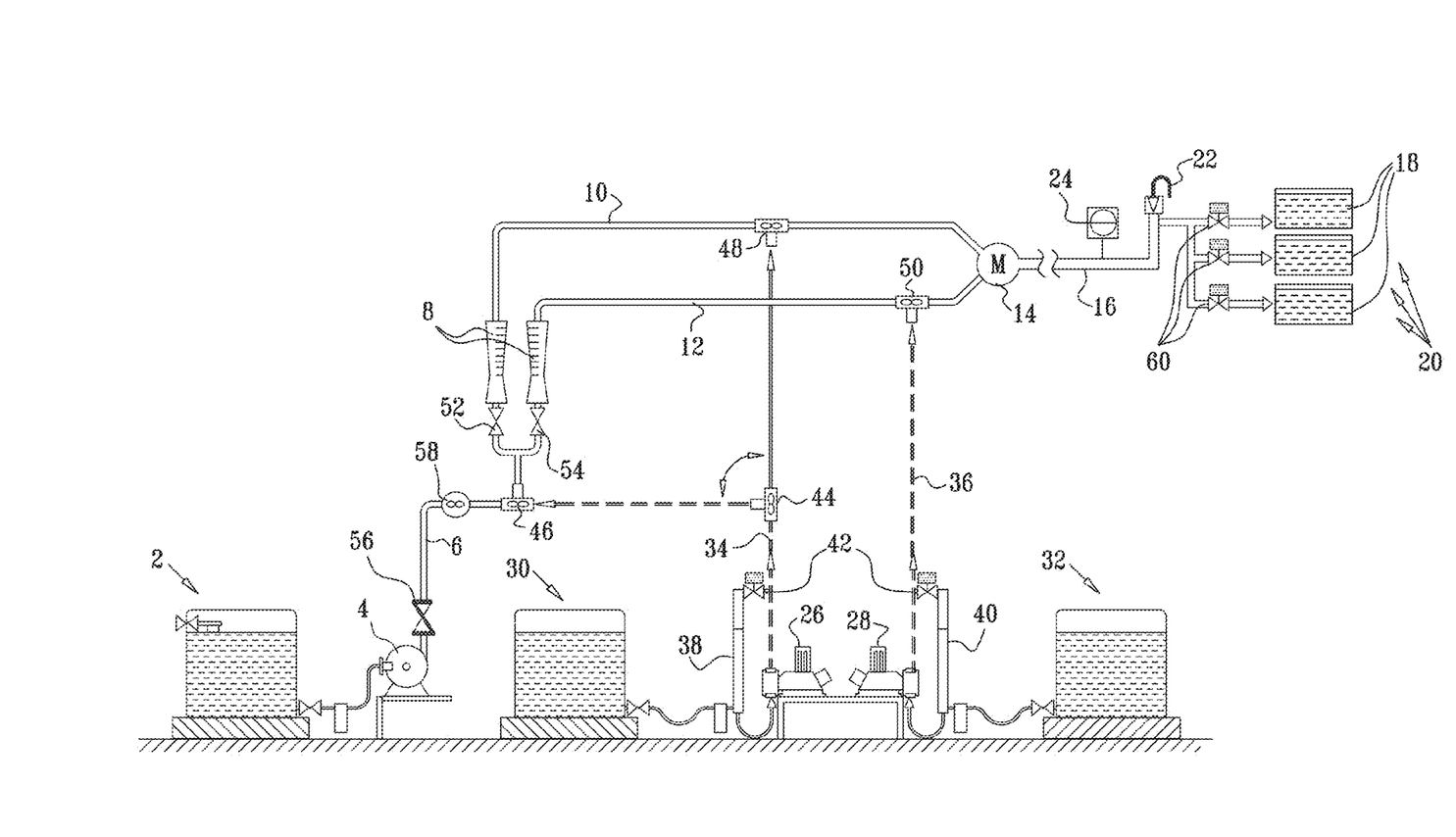
FIG. 1 is a simplified diagram of an apparatus in accordance with one embodiment of the present invention.

Reference is now made to FIG. 1, which is a simplified diagram of an apparatus for producing a biocide in accordance with an embodiment of the present invention.

As shown in FIG. 1, water is fed from a source 2, which may be a reservoir, by pump 4, via a water pipe 6 through parallel flow meters 8 and into a corresponding pair of branch lines 10 and 12, which connect to a mixer 14 which feeds common outlet pipe 16 leading to medium 18 at the locations 20. Outlet pipe 16 can be equipped with a siphon breaker 22, and may also be equipped with a control cell 24 to monitor a control parameter, such as pH, ORP, conductivity and oxygen saturation, of the biocide close to the exit of outlet pipe 16. The water from source 2 may be technical paper mill fresh water, chemically treated water, soft water, deionized water, and reclaimed process water.

Pumps 26 and 28, which may be, for example, pulsatile pumps, peristaltic pumps, venturi pumps or equivalents thereof as are known in the art, pump concentrated hypochlorite and concentrated ammonium salt, respectively, from reservoirs 30 and 32, respectively, into lines 34 and 36, respectively. Between reservoirs 30 and 32 are measuring tubes 38 and 40 and valves 42.

Line 34 contains a junction 44 for directing the flow of hypochlorite either to water pipe 6 via a junction 46 or to branch line 10 via a junction 48. Ammonium salt is fed to branch line 12 via a junction 50. These junction pieces may be, for example, simple T-connectors, or they may be in line static mixers designed to facilitate mixing of the solutions joined therewith.

When the hypochlorite solution from line 34 is directed to water pipe 6, diluted hypochlorite is fed to both branch lines 10 and 12 and the result is that the ammonium salt solution is diluted with the diluted hypochlorite. When the hypochlorite solution from line 34 is fed directly to branch line 10, the ammonium salt solution is diluted in water. Depending on the concentration of the components in reservoirs 30 and 32, the rate at which these components are pumped into lines 34 and 36 respectively, and the rate of flow of water through lines 10 and 12, the hypochlorite oxidant and nitrogen-containing compound or salt thereof may be diluted and mixed in desired proportions.

The reaction product, namely the biocide produced by the reaction of the hypochlorite and nitrogen-containing compound or salt thereof, may thus be applied directly from outlet pipe 16 into medium 18, within a brief time after the formation of the biocide. In alternative embodiments of the invention (not shown), mixer 14 is replaced by a ingress chamber or a junction piece, in which case the dilutions mix and react as they flow through outlet pipe 16, so that by the time the fluid flowing through outlet pipe 16 is introduced into medium 18, the biocide has been produced. In these alternative embodiments of the invention, outlet pipe 16 rather than mixer 14 functions as a mixing chamber. Thus the control parameter is measured immediately upon mixing.

Irrespective whether or not a mixer 14 is utilized, the flow through outlet pipe 16 should be sufficiently fast that the biocide does not have time to decompose prior to introduction into the medium 18. The length of pipe 16 can be adjusted to achieve the desired mixing time. In some embodiments of the invention, the time from which the diluted hypochlorite and diluted ammonium salt are mixed with each other to form the biocide until the biocide reaches control cell 24 is 30 seconds or less, such as 12 to 24 seconds. In other embodiments, the time is 30 to 90 seconds, such as 45 to 70 seconds. In further embodiments, the time is 90 seconds to three minutes. In still further embodiments of the invention in which the biocide is stable for more than a few minutes, the biocide may be stored (e.g. in a reservoir, not shown) prior to application to medium 18.

The control of the foregoing valves and pumps may be performed by a control system (not shown). Branch lines 10 and 12 include control valves 52 and 54, respectively, for controlling the flow rate of the water therethrough. The control system may control and monitor the supply of the water from source 2 via an electrical valve 56. Water pipe 6 may include additional control devices, such as a flow meter 58 for indicating the flow rate or flow volume. The flow of biocide to medium 18 at different locations 20 can be controlled by valves 60.

The apparatus may also be configured with alarms or other signaling devices that may give feedback to the control system. Control cell 24 in outlet pipe 16 may give feedback to the control system to enable control of biocide production in response thereto. The illustrated system may further include a timer (not shown) which is pre-settable to fix both the lengths of time for which the biocide is to be fed via outlet pipe 16 to the medium 18 to be treated, as well as the time intervals between such feedings of the biocide. The control system may also be operative to control the operation of mixer 14.

EXAMPLES

Example 1

A solution of ammonium carbonate was formed by dissolving 100 g ammonium carbonate and 50 g sodium hydroxide in 400 g water. The resulting 18% w/w solution had a density of 1.094 g/ml. A concentrated solution of sodium hypochlorite was diluted to a concentration of 5000 ppm. 4.2 ml of the ammonium carbonate solution (9.00 mmol carbonate) were mixed with 30 ml diluted hypochlorite and the resulting solution was titrated with the dilute hypochlorite. The ORP, conductivity and pH of the solution were monitored throughout the titration. Hereinafter, the procedure including diluting a concentrated ammonium salt solution in hypochlorite solution will be referred to as the "new method".

Since each mole of ammonium carbonate has two ammonium ions, the expected endpoint of the reaction is at a hypochlorite/carbonate ratio of 2. ORP reached a minimum at a ratio of 1.80 and conductivity reached a minimum at a ratio of 1.72. On the other hand, the pH maximum was not reached until a ratio of 2.58, well beyond the endpoint. Thus, it is shown that ORP and conductivity can be used as endpoint indicators at high pH, while pH is not a suitable indicator under these conditions.

A solution of ammonium carbonate was formed by dissolving 100 g ammonium carbonate in 400 g water. The resulting 20% w/w solution had a density of 1.137 g/ml. A concentrated solution of sodium hypochlorite was diluted to a concentration of 7900 ppm. 1.4 ml of the ammonium carbonate solution (3.32 mmol carbonate) were diluted in 50 ml water and the resulting solution was titrated with the dilute hypochlorite. The ORP, conductivity and pH of the solution were monitored throughout the titration. Hereinafter, the procedure including diluting a concentrated ammonium salt solution in water will be referred to as the "old method".

An ORP minimum was observed at a hypochlorite to carbonate ratio of 1.34. A pH maximum at pH=11.73 was observed at a hypochlorite/carbonate ratio of 2.01. No conductivity minimum was observed. It can be seen from here that while ORP can serve as an indicator even when the ammonium salt dilution is prepared by dilution of an ammonium salt stock solution in water, a minimum conductivity was not detected and thus conductivity is not an effective control parameter under these conditions.

Example 2—Ammonium Carbamate—New Method

Ammonium carbamate and ammonium carbonate exist in a pH-dependent equilibrium, with higher pH favoring ammonium carbamate. Since ammonium carbamate has one ammonium ion per mole while ammonium carbonate has two ammonium ions per mole, the amount of hypochlorite needed to fully react with a solution of ammonium carbamate or ammonium carbonate depends on the mixture formed between these two compounds.

A 20% stock solution of ammonium carbamate was formed by dissolving 20 g ammonium carbamate and varying amounts of sodium hydroxide in water. 5.5 ml of the ammonium carbamate stock solution was diluted with 3200 ppm or 5000 ppm sodium hypochlorite and the resulting solution was titrated with the remaining hypochlorite. The ORP, conductivity and pH of the solution were monitored throughout the titration. Table 1 shows the reaction conditions for various tests as well as the observed maximum pH and minimum ORP and conductivity.

TABLE 1

| Molar ratio NaOH:carbamate | Initial pH | Hypochlorite concentration | Hypochlorite:carbamate ratio at ORP minimum | Hypochlorite:carbamate ratio at conduc. minimum | Hypochlorite:carbamate ratio at pH maximum |
|---|---|---|---|---|---|
| 0 | 9.24 | 3200 | 2.01 | 1.60 | 2.08 |
| 0.5 | 9.74 | 3200 | 1.39 | 1.27 | 2.03 |
| 1 | 10.24 | 3200 | 0.96 | 0.90 | 1.92 |
| 1.5 | 12.34 | 3200 | | | |
| 2 | 12.42 | 3200 | | | |
| 0.5 | 12.07 | 5000 | 1.45 | 1.27 | 2.17 |
| 0.75 | 11.95 | 5000 | 1.17 | 0.99 | 1.89 |
| 0.9 | 11.87 | 5000 | 0.89 | 0.71 | 1.70 |
| 1.0 | 11.80 | 5000 | 0.62 | 0.53 | 1.41 |
| 1.1 | 11.80 | 5000 | 0.53 | 0.53 | 1.41 |
| 1.25 | 11.74 | 5000 | | | 1.24 |

It can be seen from the results in Table 1 that the amount of hypochlorite needed to complete the reaction decreases with increasing pH. This is to be expected since as the pH increases the equilibrium shifts to carbamate and there is less ammonium available. The ideal hydroxide:carbamate ratio was found to be 0.75. At this ratio, the minimum ORP and conductivity both occur at a hypochlorite:carbamate ratio of about 1. It can be seen in all of the tests that the pH maximum occurs well after the minimum ORP and conductivity, thus showing the pH is not an effective control parameter under these conditions.

Example 3—Ammonium Carbonate—New Method

A 20% stock solution of ammonium carbonate was formed by dissolving 20 g ammonium carbonate and varying amounts of sodium hydroxide in water. 5.5 ml of the ammonium carbonate stock solution were diluted with 5000 ppm sodium hypochlorite and the resulting solution was titrated with the remaining hypochlorite. The ORP, conductivity and pH of the solution were monitored throughout the titration. Table 2 shows the reaction conditions for various tests as well as the observed maximum pH and minimum ORP and conductivity.

TABLE 2

| Molar ratio NaOH:carbonate | Initial pH | Hypochlorite concentration | Hypochlorite:carbonate ratio at ORP minimum | Hypochlorite:carbonate ratio at conduc. minimum | Hypochlorite:carbonate ratio at pH maximum |
|---|---|---|---|---|---|
| 0 | 8.97 | 5000 | 1.96 | 2.07 | 2.19 |
| 0.6 | 9.35 | 5000 | 1.75 | 1.75 | 2.19 |
| 0.9 | 9.79 | 5000 | 1.53 | 1.42 | 2.08 |
| 1.1 | 10.05 | 5000 | 1.19 | 1.08 | 1.94 |

TABLE 2-continued

| Molar ratio NaOH:carbonate | Initial pH | Hypochlorite concentration | Hypochlorite:carbonate ratio | | |
|---|---|---|---|---|---|
| | | | at ORP minimum | at conduc. minimum | at pH maximum |
| 1.2 | 10.12 | 5000 | 1.06 | 0.96 | 1.92 |
| 1.3 | 10.30 | 5000 | 0.86 | 0.86 | 1.82 |
| 1.4 | 10.52 | 5000 | 0.74 | 0.84 | 1.69 |
| 1.8 | 11.97 | 5000 | 0.41 | | 2.19 |

It can be seen from the results in Table 2 that the amount of hypochlorite needed to complete the reaction decreases with increasing pH. This is to be expected since as the pH increases the equilibrium shifts to carbamate and there is less ammonium available. The ideal hydroxide:carbonate ratio was found to be 1.1-1.2. At this ratio, the minimum ORP and conductivity both occur at a hypochlorite:carbonate ratio of about 1. It can be seen in all of the tests that the pH maximum occurs well after the minimum ORP and conductivity, thus showing the pH is not an effective control parameter under these conditions.

That the ideal hydroxide ratio is higher for carbonate than for carbamate is also expected. A 1:1 ratio of hypochlorite:carbonate/carbamate is observed when all of the species are converted to carbamate. More hydroxide is required for this when starting with carbonate than when starting with carbamate. In both cases, under very high pH conditions ORP and conductivity minima were note observed. Reaction with other ammonium salts at very high pH showed the same trend, indicating that production of the biocide in very high pH is less efficient.

Example 4—Ammonium Sulfate—New Method

A 28% stock solution of ammonium sulfate was formed by dissolving 28 g ammonium sulfate in 72 ml water. 0.45 ml of the ammonium sulfate stock solution and 0.25 ml of a 33% NaOH solution were diluted in 30 ml of a 4000 ppm sodium hypochlorite solution, and the resulting solution was titrated with the remaining hypochlorite. The ORP, conductivity, pH and oxygen saturation of the solution were monitored throughout the titration.

An ORP minimum was observed at a hypochlorite/sulfate ratio of 0.78. It was at this ratio that the oxygen saturation dropped below 90%. No pH maximum or conductivity minimum was observed. It can be seen that oxygen saturation also can serve as a control parameter. It can also be seen that two control parameters can be used together to further confirm the endpoint of the reaction.

Further tests performed under different conditions show that various control parameters can be used when the correct reaction conditions are chosen. Initial pH of the diluted sulfate solution is adjusted by adding sodium hydroxide. The reaction conditions and the results are summarized in Table 3.

TABLE 3

| Hypochlorite Concentration | Initial pH | Hypochlorite to carbamate molar ratio | | |
|---|---|---|---|---|
| | | at ORP minimum | at conductivity minimum | at drop in $O_2$ saturation |
| 3290 ppm | 9.96 | 0.56 | 0.52 | 0.52 |
| 4380 ppm | 12.11 | 0.63 | 0.63 | 0.63 |

TABLE 3-continued

| Hypochlorite Concentration | Initial pH | Hypochlorite to carbamate molar ratio | | |
|---|---|---|---|---|
| | | at ORP minimum | at conductivity minimum | at drop in $O_2$ saturation |
| 5480 ppm | 10.61 | 0.63 | 0.55 | 0.55 |
| 3290 ppm | 9.88 | 0.52 | 0.47 | 0.57 |

Example 5—Ammonium Chloride—New Method

A 23% stock solution of ammonium chloride was formed by dissolving 23 g ammonium carbonate in 77 g water. 0.43 ml of the ammonium chloride stock solution and 0.25 ml of a 33% NaOH solution were diluted in 30 ml of a 4000 ppm sodium hypochlorite solution, and the resulting solution was titrated with the remaining hypochlorite. The ORP, conductivity, pH and oxygen saturation of the solution were monitored throughout the titration.

A conductivity minimum was observed at a hypochlorite/chloride ratio of 0.64. It was at this ratio that the oxygen saturation dropped below 90%. No pH maximum or ORP minimum was observed. It can be seen that using a combination of several control parameters ensures that the endpoint of the reaction can be determined by at least one control parameter.

Further tests were performed to determine the effect of hypochlorite concentration and starting pH. The pH of the diluted ammonium chloride solution was adjusted by adding sodium hydroxide. ORP, conductivity and oxygen saturation were measured during the tests. The test conditions and results are shown in Table 4.

TABLE 4

| Hypochlorite Concentration | Initial pH | Hypochlorite to carbamate molar ratio | | |
|---|---|---|---|---|
| | | at ORP minimum | at conductivity minimum | at drop in $O_2$ saturation |
| 3290 ppm | 8.91 | 1.12 | 1.00 | 1.1 |
| 3290 ppm | 10.43 | 1.32 | | 1.25 |
| 5480 ppm | 8.99 | 1.08 | 0.92 | 0.92 |
| 5480 ppm | 11.81 | 0.58 | 0.67 | 0.58 |

These results show that under very high alkalinity the biocide degrades much faster, and it is practically impossible to produce 1:1 molar ratio with no degraded biocide.

Example 6—Ammonium Sulfamate—New Method

A 20% stock solution of ammonium sulfamate was formed by dissolving 50 g ammonium sulfamate in 200 g water. 5.0 ml of the ammonium sulfamate stock solution were diluted in 30 ml of a 5800 ppm sodium hypochlorite solution, and the resulting solution was titrated with the remaining hypochlorite. The ORP, conductivity and pH of the solution were monitored throughout the titration.

A conductivity minimum was observed at a hypochlorite/sulfamate ratio of 0.94. An ORP minimum was observed at a hypochlorite/sulfamate ratio of 1.20. A pH maximum was observed at a hypochlorite/sulfamate ratio of 1.41. The discrepancy between the ORP and conductivity measurements may be due to the longer response time of the ORP electrode.

In a further test, 10 g NaOH were added to the sulfamate stock solution. In this case, both the conductivity and ORP had minima at a hypochlorite/sulfamate ratio of 0.94, while the pH maximum occurred only at a hypochlorite/sulfamate ratio of 1.95. The delay in the pH maximum is expected since the pH was higher due to the addition of NaOH and thus the system was less sensitive to the pH change caused by degradation of MCA.

Example 7—Ammonium Bromide—Old Method 1.6 ml of a 35% ammonium bromide stock were diluted in 100 ml of water to form a 5500 ppm solution of ammonium bromide. A 12% sodium hypochlorite stock was diluted in water to form solutions at concentrations of 3000 ppm (test 1), 4000 ppm (test 2) and 5000 ppm (test 3). 50 ml of the ammonium bromide solution was titrated with each of the hypochlorite dilutions. In addition, 50 ml of ammonium bromide containing 0.25 ml of a 33% NaOH solution was titrated with 4000 ppm hypochlorite (test 4). The pH, ORP, conductivity and oxygen saturation of the solution were monitored throughout the titrations. The results are shown in Table 5.

TABLE 5

| | | Hypochlorite to carbamate molar ratio | | |
|---|---|---|---|---|
| Test | Initial pH | at ORP minimum | at conductivity minimum | at drop in oxygen saturation |
| 1 | 6.47 | 1.36 | 0.74 | 0.74 |
| 2 | 6.59 | 1.07 | | 0.82 |
| 3 | 6.00 | 1.13 | | 0.82 |
| 4 | 9.46 | 0.82 | | 0.82 | pH increases slowly as the biocide is produced and decreases sharply when the degradation is significant. In all four tests, a broad range for the pH maximum was observed, rather than a sharp point, particularly in test 4 where the starting pH was high due to the addition of NaOH. The degradation sharp decrease in pH is the easiest to detect, although the maximum is the equimolar point. When the hypochlorite concentration is higher, this point becomes easier to detect, if excess NaOH is avoided. From this it can be seen that it is not sufficient to have a good detection method. The conditions for producing the biocide, such as hypochlorite concentration, should also be controlled.

An ORP minimum was seen in all tests, meaning ORP is universal as a detection and control method. The ORP minimum can form a broad range, rather than a clear sharp point. The point to control is the drop to lower ORP, even though the sharp increase in ORP due to degradation of the biocide is easier to detect. A broad minimum indicates that the reaction conditions for producing the biocide are not ideal. The biocide is degrading as it is produced, and other conditions should be chosen to produce the biocide effectively.

A conductivity minimum was observed only when using 3000 ppm hypochlorite. In order to identify a conductivity minimum, a decrease in conductivity must be observed even as hypochlorite, which adds conductivity, is added. If hypochlorite is added in big steps, the added conductivity of the hypochlorite masks the conductivity minimum, making it impossible to use conductivity for reaction control. Conductivity thus is less universal as a control parameter than ORP or pH, but it can be a more useful tool when applied properly.

Degradation of the biocide results in decrease in oxygen saturation. Since degradation consumes oxygen, this method of monitoring degradation is the most sensitive and least dependent on reaction conditions. All of the tests showed a drop in oxygen saturation, first slowly and then a sharp drop to zero. An excess of NaOH slows the degradation, but does not stop it. The degradation starts at the same value, or even slightly earlier, but it proceeds with a lower rate.

FIELD EXPERIMENTS

The general method for field experiments was a follows: A supply of soft water is provided. The water supply can be split into two streams before any reagent is added to supply water (old method), or concentrated sodium hypochlorite is mixed with the supply water to form diluted hypochlorite which is divided into two streams. Ammonium salt is added to one of the hypochlorite streams containing 10-50% of the total hypochlorite volume, and both streams are mixed in a mixing chamber (new method).

The control elements can be placed in a control cell. The cell can be placed immediately after the mixing chamber, in a short pipe reached 12-24 seconds after mixing, or at a farther point, in a long pipe reached 40-76 seconds after mixing. Measurement of pH, ORP, conductivity and oxygen saturation takes place at the control cell. In addition to monitoring results in the control cell, similar values are also measured manually at the outlet of the feeding unit, about five minutes after production of the biocide.

During the process for making the biocide one of the reagent's feed rate is fixed, while the feed rate of the other reagent is varied. Either hypochlorite or ammonium salt can be fixed. The variable feed rate can start from a lowest feed rate, and gradually increase until excess chemical is added (hereinafter "going up") or it can start from the highest feed rate, above the expected reaction end point, and gradually decrease to a low feed rate, below the expected reaction end point (hereinafter "going down"). The examples below will show the results of tests varying the defined reaction conditions.

Example 8—Comparison of Old and New Methods

Old Method:

38.7 l/h of a 10% sodium hypochlorite solution were mixed with 400 l/h of water and fed to a reaction chamber. 45.3 l/h of an 18% ammonium carbamate solution comprising 9% NaOH were mixed with 350 l/h of water and fed to the reaction chamber. The carbamate flow rate was gradually decreased to 19.3 l/h. The ORP, conductivity and pH were monitored online in the reaction chamber, and ORP and conductivity were confirmed by manually measuring samples exiting the reaction chamber.

The minimum conductivity was observed at a carbamate flow rate of 36.0 l/h, corresponding to a hypochlorite/carbamate ratio of 0.58. The minimum ORP was observed at a carbamate flow rate of 31.9 l/h, corresponding to a hypochlorite/carbamate ratio of 0.65. No pH maximum was observed.

New Method:

In an alternative study, the 10% sodium hypochlorite solution was mixed with 750 l/h of water. 400 l/h of the resulting flow was fed to the mixing chamber, and the remainder was used to dilute the 18% ammonium carbamate solution. The carbamate solution thus diluted with the hypochlorite solution was also fed to the mixing chamber. The flow rate of the 18% carbamate solution was varied as in the previous study. In this case, the minimum conductivity was observed at a carbamate flow rate of 28.3 l/h, corresponding to a hypochlorite/carbamate ratio of 0.74, and the minimum ORP was observed at a carbamate flow rate of 25.2 l/h, corresponding to a hypochlorite/carbamate ratio of 0.82. Also in this case, no pH maximum was observed.

From a comparison of these tests, it can be seen that in the old method, wherein ammonium salt is diluted in water, the control parameters indicate an end of reaction at a lower hypochlorite/carbamate ratio than in the new method. This suggests that in the old method, some biocide begins to degrade before the endpoint is reached. In addition, it was observed that the correlation between the online and manual conductivity measurements when using the new method, while when using the old method, the conductivity measurements were unstable. The new method appears to be superior in this case.

When ammonium carbonate was used as the ammonium salt, the results were somewhat different. No minimum conductivity was observed using either method, and the same ORP minimum was observed using both methods. Thus, in the case of ammonium carbonate there was no difference between the two methods.

Example 9—Variation of Feed Rates

Several tests were performed according to the general new method described in Example 8, except that in some of the tests the ammonium carbamate feed rate was constant and the hypochlorite feed rate was steadily increased (going up), while in other tests the hypochlorite feed rate was kept constant and the feed of ammonium carbamate steadily increased (going up) or decreased (going down). The hypochlorite concentration was 6000 ppm. Table 6 summarizes the basic conditions and results for each test. The percent of the total water flow used to dilute the ammonium carbamate is given as % flow to ammonium.

TABLE 6

| % flow to ammonium | Varying | Going | Hypochlorite:carbamate at min. ORP | Hypochlorite:carbamate at min. conductivity |
|---|---|---|---|---|
| 46.6 | Ammonium | Up | 0.66 | 0.66 |
| 46.6 | Ammonium | Down | 0.62 | 0.57 |
| 33.3 | Ammonium | Up | 0.70 | 0.59 |
| 33.3 | Ammonium | Down | 0.62 | 0.56 |
| 20 | Ammonium | Up | 0.70 | 0.66 |
| 35 | Hypochlorite | Up | 1.16 | |
| 50 | Hypochlorite | Up | 1.20 | |
| 80 | Hypochlorite | Up | 1.33 | |

The results in Table 6 show that a minimum ORP can be detected using all of the following options: maintaining the ammonium carbamate feed rate fixed and increasing the hypochlorite feed rate gradually, or maintaining the hypochlorite feed rate fixed, and increasing or decreasing ammonium carbamate feed rate, though the values for minimum ORP were different. Tests conducted with a fixed feed of ammonium carbamate and variable feed of hypochlorite show higher ORP minima, at a molar ratio of hypochlorite:carbamate higher than 1 indicating that some ammonium carbamate converted to ammonium carbonate during the process.

Minimum conductivity was clearly seen when tests were conducted with a fixed feed rate of hypochlorite, and a variable feed rate of ammonium carbamate. There was no significant difference between increasing or decreasing the carbamate feed. No minimum conductivity was detected when tests were conducted with a fixed feed rate of ammonium carbamate, and a variable feed of hypochlorite. The increase in conductivity due to addition of hypochlorite to ammonium carbamate apparently masks the conductivity minimum at the end point. The end point may nonetheless be observed if the hypochlorite feed is increased very slowly.

Example 10—Variation of Split of Flow

Several tests were performed according to the general new method described in Example 8, except that the percent of the total water flow used to dilute the ammonium carbamate was different in each test. Table 7 summarizes the basic conditions and results for each test.

TABLE 7

| % flow to ammonium | Hypochlorite:carbamate at min. ORP | Hypochlorite:carbamate at min. conductivity |
|---|---|---|
| 46.6 | 0.82 | 0.73 |
| 10 | 0.82 | 0.82 |
| 46.6 | 0.62 | 0.57 |
| 33.3 | 0.62 | 0.56 |

The results presented in Table 7 show that the best results are measured using 10% of the total volume of water to dilute the ammonium salt, as the measurements for ORP and conductivity are equal.

Example 11—Variation of Holding Time

Several tests were performed according to the general new method described in Example 8, except that the holding time from leaving the mixing chamber until arriving at the control cell was different in each test. The different holding times were achieved by using different flow rates and using a long or short pipe. Table 8 summarizes the basic conditions and results for each test.

The conductivity online and manual minima are similar in most of the tests. The differences between online and manual ORP readings are much bigger than the differences in conductivity. This highlights one disadvantage of ORP that the electrode takes time to stabilize. Thus online readings may not be as accurate as manual readings. The high ORP values at a shortest contact time may prove that the reaction is not completed at that point yet.

TABLE 8

| Pipe | Holding time (sec) | Hypochlorite:carbamate at min. ORP | | Hypochlorite:carbamate at min. conductivity | |
|---|---|---|---|---|---|
| | | Online | Manual | Online | Manual |
| Short | 16 | 0.68 | 0.75 | 0.75 | 0.75 |
| Long | 50 | 0.67 | 0.75 | 0.61 | 0.67 |
| Long | 50 | 0.70 | 0.77 | 0.85 | 0.77 |
| Short | 12 | 0.77 | 0.77 | 0.99 | 0.77 |
| Short | 16 | 0.68 | 0.75 | 0.75 | 0.75 |
| Long | 50 | 0.62 | 0.65 | 0.57 | 0.59 |
| Short | 16 | 0.70 | 0.77 | 0.70 | 0.70 |
| Short | 12 | 0.70 | 0.77 | 0.99 | 0.99 |
| Long | 40 | 0.76 | 0.76 | 0.76 | 0.69 |

Even though the ORP values depend significantly on the holding time, the molar ratio shows a lower variability, and the ratio decreases only slightly as the holding time increases. This shows that a holding time is very useful, and a longer holding time is better than a short holding time.

Example 12—Variation of Hypochlorite Concentration

Varying amounts of a 7% sodium hypochlorite solution were mixed with 800 l/h of water. 400 l/h of the resulting flow was fed to the mixing chamber, and the remainder was used to dilute an 18% ammonium carbamate solution. The carbamate solution thus diluted with the hypochlorite solution was also fed to the mixing chamber. The stroke of the ammonium salt pump was varied in order to change the flow rate of the carbamate. pH, ORP and conductivity were measured online. Conductivity was measured using two different electrodes, a standard conductivity electrode and an inductive electrode.

The procedure described above was repeated for three different hypochlorite concentrations, 3700 ppm (test 1), 4400 ppm (test 2) and 4800 ppm (test 3). No pH maximum was observed in any of the tests. In test 1, no ORP or conductivity minima were observed.

In test 2, the ORP minimum occurred at a pump stroke of 50%, corresponding to a carbamate flow rate of 17.3 l/h and a hypochlorite to carbamate ratio of 1.17. Both conductivity electrodes showed minima at a pump stroke of 55%, corresponding to a carbamate flow rate of 19.6 l/h and a hypochlorite to carbamate ratio of 1.03. In test 3, the ORP minimum occurred at a pump stroke of 55%, corresponding to a carbamate flow rate of 19.6 l/h and a hypochlorite to carbamate ratio of 1.14. Both conductivity electrodes showed minima at a pump stroke of 60%, corresponding to a carbamate flow rate of 22.0 l/h and a hypochlorite to carbamate ratio of 1.02.

When ammonium carbamate is added to water, the ORP increases. When ammonium carbamate is added to hypochlorite and biocide is produced, the ORP decreases until the hypochlorite is exhausted, at which point no more biocide is produced and the ORP begins to rise again. When the biocide is produced as described in this Example and the concentration of hypochlorite is low, the trend of ORP mimics that of addition of ammonium carbamate to water, and no ORP minimum is detected. Increasing the hypochlorite concentration and producing more biocide will reveal the expected ORP minimum.

Conductivity follows a similar trend as ORP. When the concentration of hypochlorite is low and only a small amount of biocide is produced, the decrease in conductivity due to the production of the biocide is masked by the increase in conductivity due to the addition of ammonium carbamate. Thus no minimum is observed. The minimum can be brought out by increasing the concentration of hypochlorite. In addition, the minimum is more easily detected by keeping the hypochlorite concentration fixed and varying the ammonium concentration.

In an additional set of tests, the concentration of hypochlorite was the same in each test, but the fixed flow rate of hypochlorite was different in each test. The flow rate of ammonium carbamate was varied in each test to find the ideal ratio. The results are summarized in Table 9. It is again seen that too little hypochlorite in the system leads to masking of the equimolar point defined by the ORP or conductivity minima.

TABLE 9

| Hypochlorite flow rate (l/h) | Hypochlorite to carbamate molar ratio | | |
|---|---|---|---|
| | at ORP minimum | at conductivity minimum | at induction minimum |
| 45.6 | | | |
| 54 | 1.17 | 1.03 | 1.02 |
| 60 | 1.14 | 1.03 | 1.02 |

These tests prove that many factors affect the efficiency of producing a monochloramine biocide. The temperature, duration of addition and mixing of the chemicals, the initial alkalinity, the quality of the ammonium salt and accuracy of its assumed concentration, the quality of hypochlorite and changes in quality that occur during dilution and production of the biocide all may contribute to the efficient production of a biocide without degradation. Control is required to produce the biocide at its optimal yield, without degradation, under variable conditions.

Oxidation-reduction potential, ion concentration as measured by conductivity or induction or TDS, and oxygen saturation can be used to control the biocide production. Looking at the results of the tests above, it is seen that sometime there is no ORP minimum, or no conductivity minimum, or both are missing. By varying the reaction conditions, most importantly the relative concentration of the reagents, the minima can be seen or they can disappear.

It will be appreciated by persons skilled in the art that the present invention is not limited to what has been particularly shown and described hereinabove. Rather the scope of the present invention includes both combinations and subcombinations of various features described hereinabove as well as modifications thereof which would occur to a person of skill in the art upon reading the foregoing description and which are not in the prior art.

The invention claimed is:

1. A method for producing a biocide comprising:
mixing a solution of a hypochlorite oxidant with a solution of an ammonium salt to produce a biocide; and
monitoring a control parameter that indicates when a maximum yield of said biocide, which yield is attainable without degradation of said biocide, has been reached;
wherein the control parameter has a) a fixed value that changes only after said yield has been reached; or b) a variable value that has a maximum, a minimum or an inflection at the point when said yield has been reached;
wherein said control parameter is selected from the group consisting of oxidation-reduction potential (ORP), conductivity, induction and oxygen saturation.

2. The method according to claim 1, wherein said hypochlorite oxidant is sodium hypochlorite.

3. The method according to claim 1, wherein said ammonium salt is selected from the group consisting of ammonium carbonate and ammonium carbamate.

4. The method according to claim 1, wherein said solution of an ammonium salt is prepared by diluting a commercial stock solution of about 15-50% with water or with said solution of a hypochlorite oxidant immediately prior to use.

5. The method according to claim 1, wherein said control parameter is ORP.

6. The method according to claim 1, wherein said control parameter is conductivity or induction.

7. The method according to claim 1, wherein said control parameter is oxygen saturation.

8. The method according to claim 1, wherein said method comprises:
provinding a discrete amount of said solution of an ammonium salt;
adding a plurality of discrete amounts of said solution of a hypochlorite oxidant to said discrete amount of said solution of an ammonium salt under mixing conditions; and
measuring said control parameter after the addition of each discrete amount of said solution of a hypochlorite oxidant.

9. The method according to claim 1, wherein said method comprises:
mixing a stream of a hypochlorite solution with a stream of an ammonium salt solution in a mixing chamber at a starting ratio;
holding the flow rate of one of said streams constant and gradually increasing or decreasing the flow rate of the other of said streams; and
monitoring the value of said control parameter in a stream leaving said mixing chamber.

10. A method of producing a biocide, comprising:
providing a solution of a hypochlorite oxidant;
providing a solution of an ammonium salt;
diluting said solution of an ammonium salt with a portion of said solution of a hypochlorite oxidant to form an ammonium salt dilution;
mixing the remainder of said solution of a hypochlorite oxidant with said ammonium salt dilution; and
monitoring a control parameter that indicates when a maximum yield of said biocide, which yield is attainable without degradation of said biocide, has been reached;
wherein the control parameter has a) a fixed value that changes only after said yield has been reached; or b) a variable value that has a maximum, a minimum or an inflection at the point when said yield has been reached;
wherein said control parameter is selected from the group consisting of oxidation-reduction potential (ORP), conductivity, induction and oxygen saturation.

11. The method according to claim 10, wherein said hypochlorite oxidant is sodium hypochlorite.

12. The method according to claim 10, wherein said ammonium salt is selected from the group consisting of ammonium carbonate and ammonium carbamate.

13. The method according to claim 10, wherein said control parameter is ORP.

14. The method according to claim 10, wherein said control parameter is conductivity or induction.

15. The method according to claim 10, wherein said control parameter is oxygen saturation.

16. The method according to claim 10, wherein said method comprises:
adding a plurality of discrete amounts of said solution of a hypochlorite oxidant to said ammonium salt dilution under mixing conditions; and
measuring said control parameter after the addition of each discrete amount of said solution of a hypochlorite oxidant.

17. The method according to claim 10, wherein said method comprises:
mixing a stream of a hypochlorite solution with a stream of said ammonium salt dilution in a mixing chamber at a starting ratio;
holding the flow rate of one of said streams constant and gradually increasing or decreasing the flow rate of the other of said streams; and
monitoring the value of said control parameter in a stream leaving said mixing chamber.

18. Apparatus for producing a biocide comprising:
a reservoir containing a solution of a hypochlorite oxidant;
a reservoir containing a solution of an ammonium salt;
a mixing chamber for mixing said hypochlorite oxidant with said ammonium salt to form a biocide; and
a control cell for monitoring a control parameter that indicates when a maximum yield of said biocide, which yield is attainable without degradation of said biocide, has been reached;
wherein the control parameter has a) a fixed value that changes only after said yield has been reached; or b) a variable value that has a maximum, a minimum or an inflection at the point when said yield has been reached;
wherein said control parameter is selected from the group consisting of oxidation-reduction potential (ORP), conductivity, induction and oxygen saturation.

19. The apparatus according to claim 18, wherein said hypochlorite oxidant is sodium hypochlorite.

20. The apparatus according to claim 18, further comprising:
a water source;
a conduit wherein said solution of a hypochlorite oxidant is mixed with said water to form a hypochlorite dilution, said conduit coupled to said mixing chamber; and
a conduit wherein said solution of an ammonium salt is mixed with said water or with said hypochlorite dilution to form an ammonium salt dilution, said conduit coupled to said mixing chamber.

21. The apparatus according to claim 18, wherein said ammonium salt is selected from the group consisting of ammonium carbonate and ammonium carbamate.

22. The apparatus according to claim 18, wherein said control parameter is ORP.

23. The apparatus according to claim 18, wherein said control parameter is conductivity or induction.

24. The apparatus according to claim 18, wherein said control parameter is oxygen saturation.

25. The apparatus according to claim 18, further comprising a control unit configured to:
hold the flow rate of one of said hypochlorite oxidant and said ammonium salt constant and gradually increase or decrease the flow rate of the other one of said hypochlorite oxidant and said ammonium salt;
monitor the value of said control parameter of said biocide; and
adjust the flow rate of said hypochlorite oxidant or said ammonium salt to attain a maximum yield of said biocide, which yield is attainable without degradation of said biocide.

26. Apparatus for producing a biocide, comprising:
a reservoir containing a solution of a hypochlorite oxidant;
a reservoir containing a solution of an ammonium salt;
a water source;
a conduit for mixing said solution of a hypochlorite oxidant solution with said water to form a hypochlorite dilution;
a conduit for mixing said solution of an ammonium salt with a portion of said hypochlorite dilution to form an ammonium salt dilution;
a mixing chamber for mixing a portion of said hypochlorite dilution with said ammonium salt dilution to form a biocide; and a control cell for monitoring a control parameter that indicates when a maximum yield of said biocide, which yield is attainable without degradation of said biocide, has been reached;

wherein the control parameter has a) a fixed value that changes only after said yield has been reached; or b) a variable value that has a maximum, a minimum or an inflection at the point when said yield has been reached;

wherein said control parameter is selected from the group consisting of oxidation-reduction potential (ORP), conductivity, induction and oxygen saturation.

27. The apparatus according to claim 26, wherein said hypochlorite oxidant is sodium hypochlorite.

28. The apparatus according to claim 26, wherein said ammonium salt is selected from the group consisting of ammonium carbonate and ammonium carbamate.

29. The apparatus according to claim 26, wherein said control parameter is ORP.

30. The apparatus according to claim 26, wherein said control parameter is conductivity or induction.

31. The apparatus according to claim 26, wherein said control parameter is oxygen saturation.

32. The apparatus according to claim 26, further comprising a control unit configured to:

hold the flow rate of one of said hypochlorite dilution and said ammonium salt dilution constant and gradually increase or decrease the flow rate of the other one of said hypochlorite dilution and said ammonium salt dilution;

monitor the value of said control parameter of said biocide; and adjust the flow rate of said hypochlorite oxidant or said ammonium salt to attain a maximum yield of said biocide, which yield is attainable without degradation of said biocide.

* * * * *